United States Patent [19]

Idemoto et al.

[11] Patent Number: 5,188,102
[45] Date of Patent: Feb. 23, 1993

[54] SURGICAL ULTRASONIC HORN

[75] Inventors: Morito Idemoto; Yasuo Noguchi, both of Yokohama, Japan

[73] Assignee: Sumitomo Bakelite Company Limited, Tokyo, Japan

[21] Appl. No.: 698,229

[22] Filed: May 10, 1991

[30] Foreign Application Priority Data

| May 11, 1990 | [JP] | Japan | 2-048599[U] |
| May 11, 1990 | [JP] | Japan | 2-048600[U] |
| Jun. 21, 1990 | [JP] | Japan | 2-064952[U] |

[51] Int. Cl.$^5$ .................. A61B 17/00; A61B 17/32
[52] U.S. Cl. .................. 128/24 AA; 604/22; 606/45; 606/169; 606/170
[58] Field of Search .......... 128/24 AA; 604/22; 606/45, 167, 169, 170; 433/119; 239/102.2, 589.1

[56] References Cited

U.S. PATENT DOCUMENTS

| 1,983,601 | 12/1934 | Conn | 604/22 |
| 3,086,288 | 4/1963 | Balamuth et al. | |
| 3,526,219 | 9/1970 | Balamuth | 433/119 |
| 4,169,984 | 10/1979 | Parisi | 128/24 AA |
| 4,188,952 | 2/1980 | Loschilov et al. | 606/170 |
| 4,428,748 | 1/1984 | Peyman et al. | 433/119 |
| 4,844,064 | 7/1989 | Thimsen et al. | 606/170 |
| 4,886,491 | 12/1989 | Parisi et al. | 604/22 |
| 5,026,387 | 6/1991 | Thomas | 128/24 AA |
| 5,042,461 | 8/1991 | Inoue et al. | 604/22 |
| 5,058,570 | 10/1991 | Idemoto et al. | 128/24 AA |
| 5,112,300 | 5/1992 | Ureche | 128/24 AA |

FOREIGN PATENT DOCUMENTS

| 8103125 | 11/1981 | European Pat. Off. | 604/22 |
| 139753 | 8/1985 | European Pat. Off. | |
| 9005493 | 5/1990 | European Pat. Off. | 606/170 |
| 4739197 | 10/1972 | Japan . | |
| 1388002 | 4/1988 | U.S.S.R. | 604/22 |
| 1457544 | 12/1976 | United Kingdom . | |

Primary Examiner—Lee S. Cohen
Assistant Examiner—K. M. Pfaffle
Attorney, Agent, or Firm—Browdy and Neimark

[57] ABSTRACT

A surgical ultrasonic horn used in a surgical operation comprises a horn body and an end plate portion. Cutting portions are provided on an edge and an end of the end portion. A passage for irrigation solution extends in the horn body and the end plate portion. At least one bore opens at the cutting portions by a jet angle of 5° to 90° in respect of a plane of the end plate portion. The irrigation solution passage communicates with the bore, thereby the irrigation solution is sprayed therethrough.

21 Claims, 7 Drawing Sheets (PRIOR ART)

(PRIOR ART)

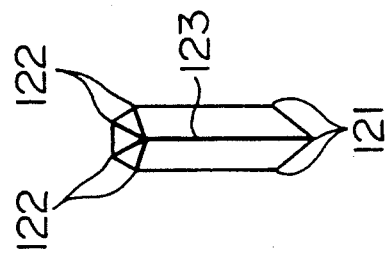
FIG. 11A
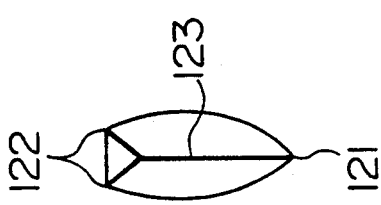
FIG. 11B
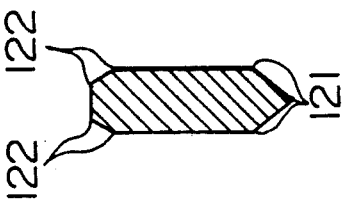
FIG. 12A
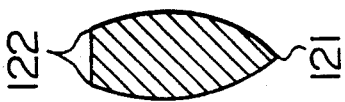
FIG. 12B
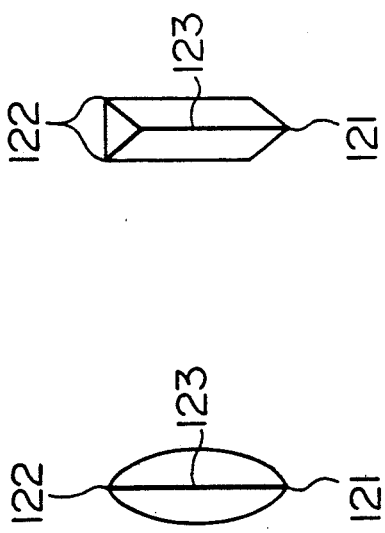
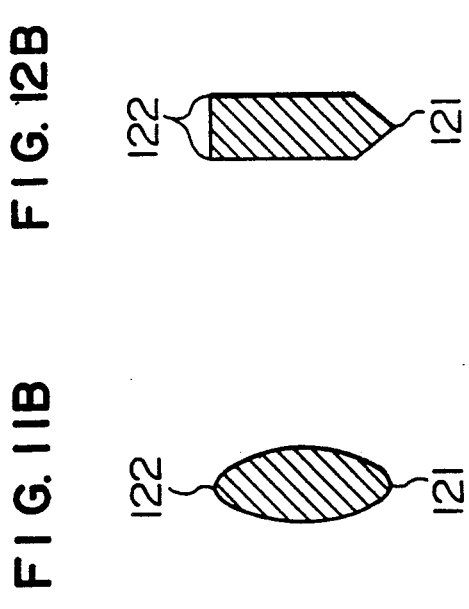

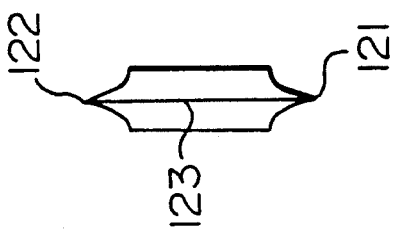
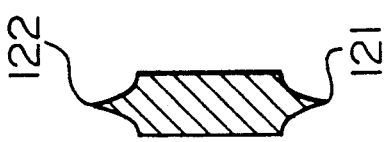
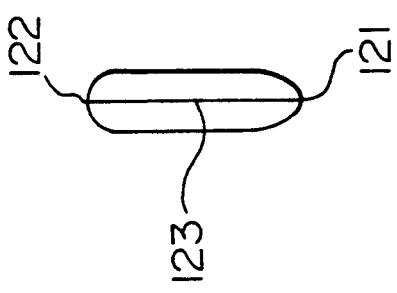
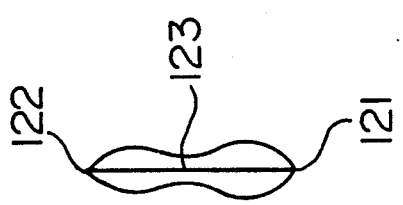

SURGICAL ULTRASONIC HORN

FIELD OF THE INVENTION AND RELATED ART STATEMENT

The present invention relates to a surgical ultrasonic horn. These horns are generally used in cutting and separating of the living tissue, e.g. cartilaginous tissue or bone.

A surgical knife has been widely used for this purpose. However, the surgical knife is inferior in cutting efficiency. Therefore, it prolongs surgery and tires the surgeon. Further, the surgeon is required to have a higher level of cutting skill.

Some surgical tools using an ultrasonic element have been proposed. For example, in the surgical tool disclosed in Japanese Patent Examined Publication No. 47-39197, an ultrasonic oscillating element having a flat end pounds a surface of the tissue against which it is placed. Therefore, the part of tissue pounded is crushed and emulsified and then removed outside. However, such surgical tool isn't appropriate for cutting and separating of tissue.

Further, another surgical tool uses an ultrasonic oscillator provided at a distal end thereof with a saw portion. In operation thereof, the ultrasonic oscillation generates frictional heat between the distal end and the tissue to be cut to raise the temperature at that point to some hundreds ° C. Accordingly, the cut part of tissue is carbonized, and the distal end of the oscillator may deteriorate and then may be broken.

OBJECT AND SUMMARY OF THE INVENTION

Accordingly, an object of the present invention is to provide a surgical tool using an ultrasonic element which is adapted to cut and separate tissue with a minimum generation of frictional heat.

The function and the advantages of the present invention will be apparent from the following explanation of the preferred embodiments described with reference to the accompanying drawings attached hereto.

BRIEF DESCRIPTION OF THE DRAWINGS

FIGS. 11A to 17A are front views showing the embodiments of different shapes of the cutting portion, respectively; and · FIGS. 11B to 17B are sectional views of the embodiments shown in FIGS. 11A to 17A, respectively.

DETAILED DESCRIPTION OF PREFERRED EMBODIMENTS

Figure 1:
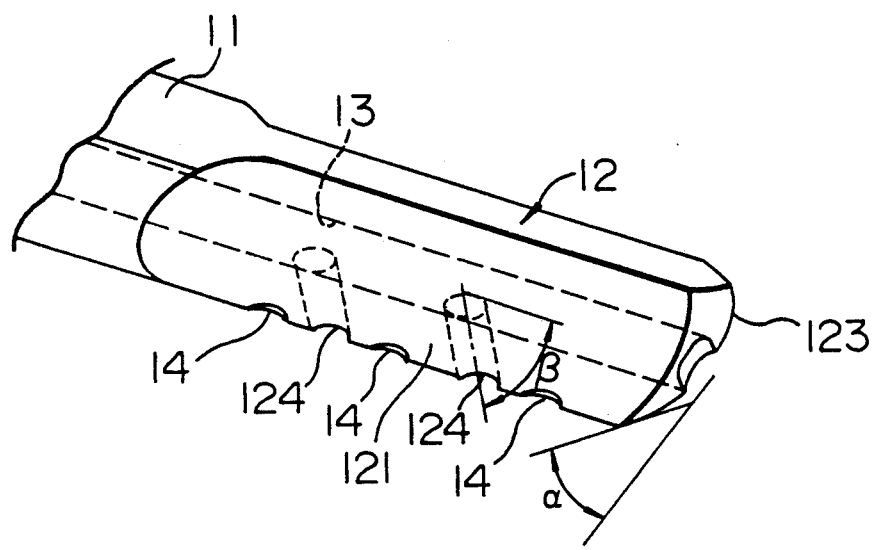
FIG. 1 is an enlarged fragmentary perspective view showing an ultrasonic horn according to a first embodiment of the present invention.
Figure 2:
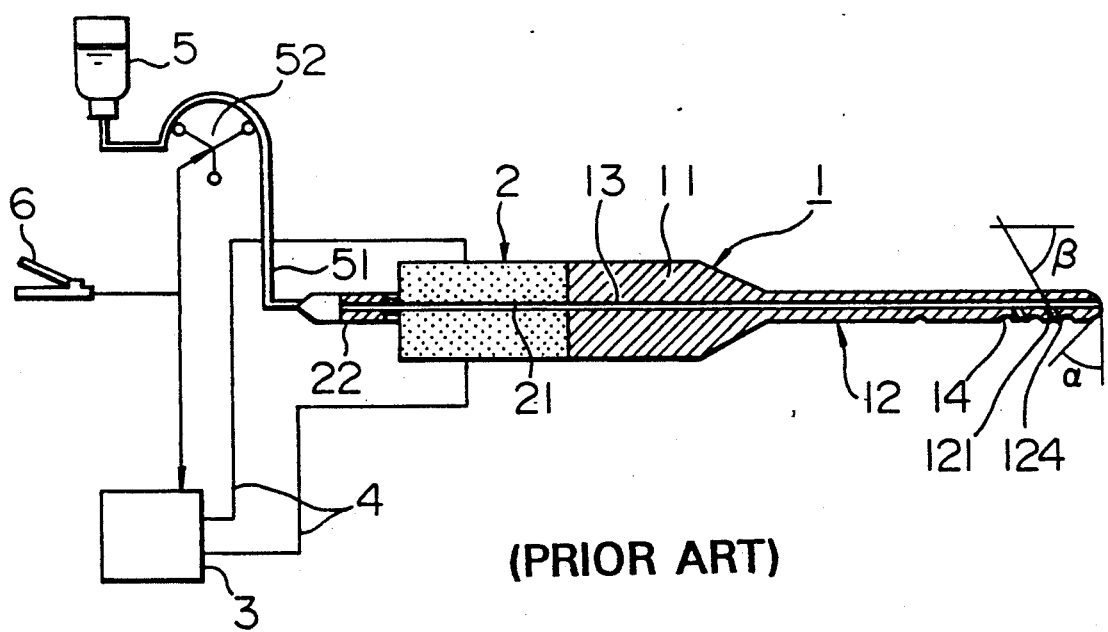
FIG. 2 is a surgical operating apparatus using the horn shown in FIG. 1.

An ultrasonic horn 1 shown in FIG. 1 is connected to an ultrasonic oscillation source 2 as shown in FIG. 2 so as to cooperate therewith. The ultrasonic oscillation source 2 is electrically connected to an ultrasonic oscillator 3 through cables 4.

The ultrasonic oscillation source 2 is provided with a through bore 21 through which an irrigation solution flows. The bore 21 is communicated at one end thereof to a reservoir 5 containing physiological saline through a tube 51 and a nipple 22 mounted to the ultrasonic oscillation source 2. A roller pump 52 is disposed in a mid portion of the tube 51 so as to pump the physiological saline.

A foot switch 6 synchronizes the ultrasonic oscillator 3 and the roller pump 52.

As shown in FIG. 1, the ultrasonic horn 1 includes a horn body 11 connected at one end thereof to the ultrasonic oscillation source 2 (as shown in FIG. 2) and a plate-like working portion 12 connected at one end thereof to the other end of the horn body through a tapered or frustoconical intermediate portion. They are integrated with each other. Cutting portions 121 and 123 are provided at one edge and an end of the end portion 12, respectively. The horn 1 is provided with an internal passage 13 through which the irrigation solution flows. The passage 13 is communicated at one end thereof with the bore 21 and the other end thereof is opened at the end of the working portion 12. The cutting portion 121 presents an edge of the elongate plate-like shape. In order to improve the cutting efficiency, the cutting portion 123 is rounded and is tapered by a slant angle $\alpha(\alpha \geq 45°)$ in respect of the oscillation direction. A plurality of recesses 14 are provided on the cutting portion 121. Further, a plurality of jet bores 124 for irrigation solution are provided on the cutting portion 121. The jet bore 124 is opened at the cutting portion 121 by a jet angle $\beta(\beta \geq 5°)$ in respect of an extending direction of the passage 13.

Next, an operation of the above explained apparatus will be described hereinunder.

At first, the foot switch is closed to operate the ultrasonic oscillator 3 and the roller pump 52. The roller pump 52 supplies physiological saline from the reservoir 5 through the tube 51, the nipple 22 and the through bore 21 of the ultrasonic oscillation source 2 to the passage 13. Simultaneously the ultrasonic oscillator 3 drives the ultrasonic oscillation source 2 to mechanically oscillate the horn 1. As a result, the cutting portions 121 and 123 cut and separate the tissue. During this operation, physiological saline is sprayed through the jet bores 124 towards and onto the tissue portion to be cut. The physiological saline suppresses the raising of temperature due to the frictional heat in the cutting portions 121, 123 and the tissue portion to be cut, thereby preventing the cutting portions 121 and 123 from deteriorating and the tissue portion to be cut from being carbonized. In the case where the irrigation solution sprayed is at 10° C. to 25° C., the temperature of the tissue portion to be cut is maintained at about 15° C. to about 30° C. Further, the jets of physiological saline can remove fine particles of the cut tissue from the surface of the tissue to expose new tissue surface to the surgeon. According this, the operation efficiency is further improved. Further, the jets of physiological saline stimulate the osteoblast on the bone and then promote the recovery of the cut portion.

Figure 3:
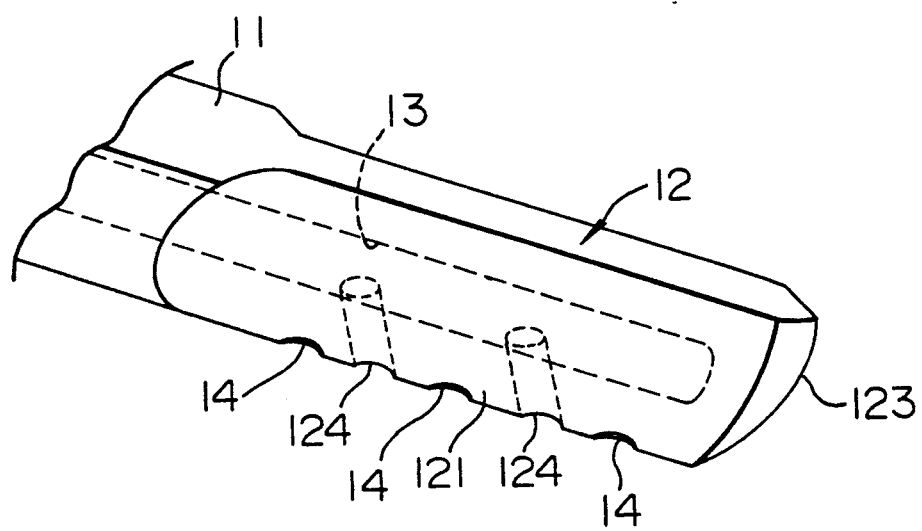
FIGS. 3 to 7C are fragmentary perspective views showing a second to a seventh embodiments of the present invention, respectively.
Figure 4:
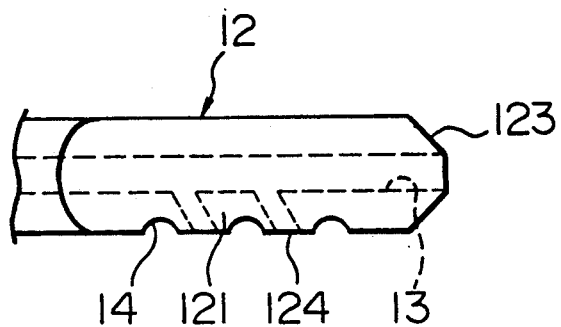

In order to obtain a suitable jet of physiological saline, it is preferable that the diameters of the jet bores 124 and the opening at the end of the working portion 12 are equal or smaller than a diameter of the passage 13. In case that the jets of physiological saline may restrict a visual field of the operation, it would be preferable to prevent the passage 13 from extending to the end of the working portion 12 as shown in FIG. 3.

In the illustrated embodiment, the recess 14 has a semispherical shape. However, another shapes may be applicable according to the circumstances. The radius of the recess 14 is between 0.3 mm and 2.5 mm. A depth is between 0.1 mm and 2 mm, preferably between 0.5 mm and 1.5 mm. The pitch between the recesses is between 1.5 mm and 7 mm, preferably between 2 mm and 3 mm. Due to the semispherical recesses, the cutting portion 121 isn't broken even though the ultrasonic oscillation of a higher amplitude of 100 μm to 300 μm is applied. since the contact resistance between the bone and the cutting portions is reduced, the cutting efficiency is improved by 20% to 30% as compared with cutting portions without recesses.

In accordance with another variation as shown in FIG. 14, the cutting portion 123 is defined by linear boundaries. The slant angle α is 45° or more, preferably 60° to 90°. The thickness of the cutting portion 123 is between 0.1 mm and 7.0 mm, preferably between 0.2 mm and 1.5 mm.

The contour of the intermediate portion between the horn body 11 and the working portion 12 may be an arc, a caternary, exponential, or Fourier curve, instead of the flat tapered or frustoconical one shown in FIG. 2.

The material of the horn is preferably titanium alloy, or stainless alloy, or a composition of titanium alloy and stainless alloy. It may be possible to apply a coating or abrasion resistance process to the cutting portions.

According to the present invention, on the cutting and separating of the bone, due to the shape of the cutting portions specified above, the cutting portions smoothly enters from the surface of the bone to an interior thereof by means of the mechanical ultrasonic oscillation when it contacts slightly against the bone. Therefore, any scattering of bone against the surgeon is suppressed, thereby enabling the operation to proceed with greater precision. The elastic tissue of the bone, e.g. periosteum is never damaged by the horn 1 due to the characteristics of the ultrasonic.

Figure 5:
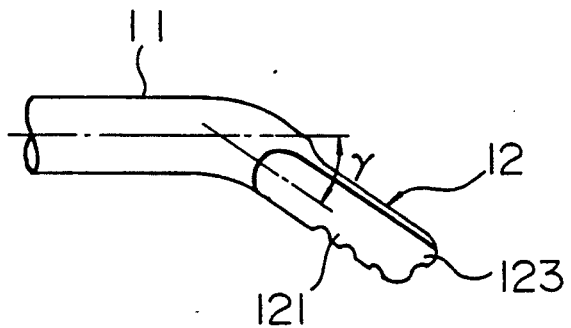

The embodiment shown in FIG. 5 is suitable for the cutting operation in the case that the visual field is restricted. The working end portion 12 is bent by an angle γ in respect of an axis of the horn body 11. The angle γ is preferably between 10° and 30°.

Figure 6A:
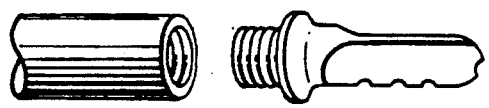
Figure 6B:
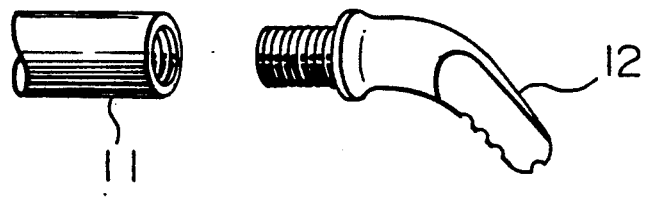

In the embodiments shown in FIGS. 6A and 6B, the end portion is detachably screw-mounted to the horn body. In this case, the working end portion must be so mounted to the horn body that the axis of the horn body extends within a plane including the cutting portions 121 and 123.

Figure 7:
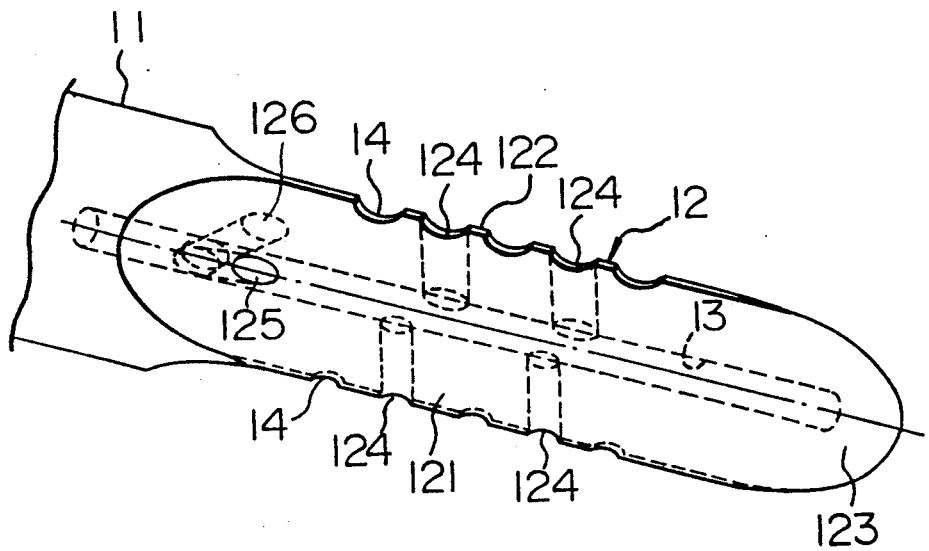
Figure 7A:
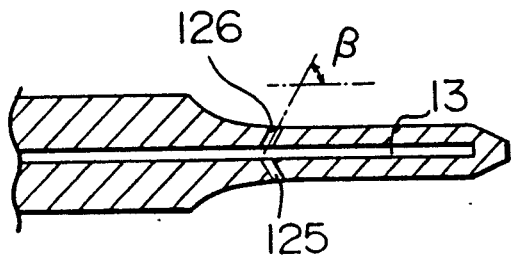
Figure 7B:
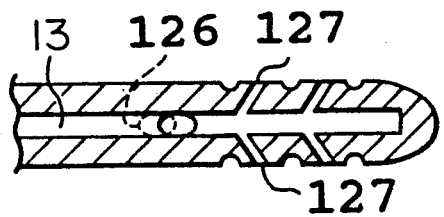
Figure 7C:
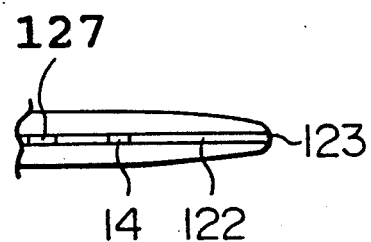
Figure 8:
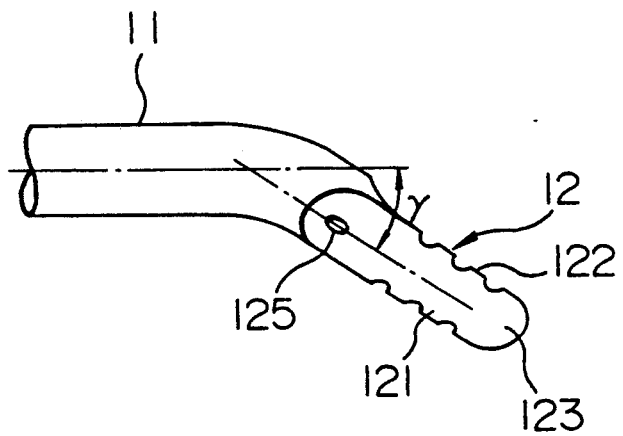
FIGS. 8 to 10 are fragmentary perspective views showing horns modified from one shown in FIG. 7.
Figure 9:
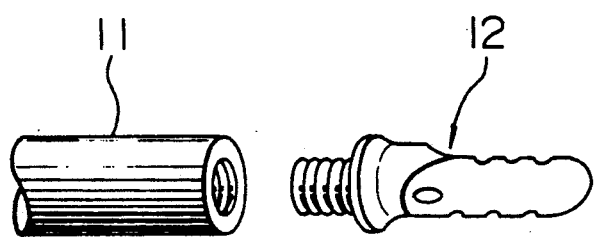
Figure 10:
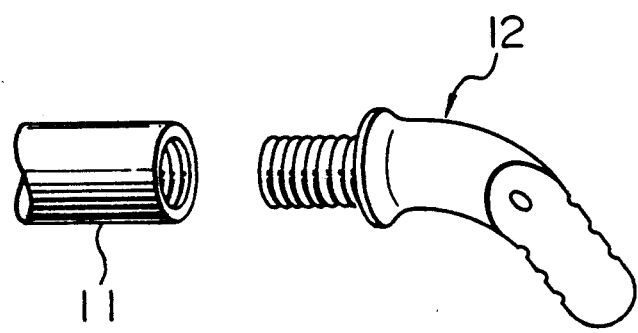

In the embodiment shown in FIG. 7, the working portion 12 is provided at opposite edges thereof with a first and a second cutting portions 121, 122, and at the end thereof with a third cutting portion 123. The irrigation solution passage 13 doesn't extend to the end of the end portion in the illustrated embodiment of FIG. 7, though it can be modified open at the end of the end portion. A pair of irrigation solution jet bores 125 and 126 open at a proximal portion of the working portion 12 by the jet angle β(β≧5°) in respect of the extending direction of the irrigation solution passage 13, respectively (FIG. 7A). A plurality of other jet bores 127 open at the cutting edges 121 and 122, respectively (FIGS. 7B and 7C). There may be some modifications as shown in FIGS. 8 to 10. Namely, the working portion 12 is bent by an anger γ in respect of the axis of the horn body 11 and/or is detachably screw-mounted to the horn body 11.

The cutting portions of the embodiments shown in FIGS. 11A to 17B are different from one another. The cutting portions 121 and 122 extend parallel to the direction of the ultrasonic oscillation. On the contrary, the cutting portion 123 has linear boundaries which extend so as to cross the oscillation direction, namely extend in a direction which crosses the oscillation direction by an angle α not zero. The cutting portion 123 may have an arc contour.

What is claimed is:

1. A surgical ultrasonic horn adapted to be driven by an ultrasonic oscillation source, comprising:
    a horn body extending along an axis and having a proximal end and a distal end, said proximal end being adapted to be connected to the ultrasonic oscillation source;
    a plate-like working portion ext ending from the distal end of said horn body, said working portion being provided along a first edge with a first cutting portion and along an end thereof with a second cutting portion;
    a first recess being provided in said first cutting portion;
    a passageway extending through said horn body and said working portion, and adapted to be communicated with a liquid source for the passage therethrough of liquid; and
    a first bore communicating with said passageway and opening by a jet angle of 5° to 90° in respect of the axis of said horn body, said first bore constituting means for spraying liquid passing from said passageway.

2. A horn according to claim 1, wherein said passageway opens at said end of said working portion.

3. A horn according to claim 1, wherein said working portion is bent with respect to said axis of said horn body by an angle not greater than 90°.

4. A horn according to claim 1, wherein said second cutting portion provided at the end of said working portion is rounded.

5. A horn according to claim 1, wherein said second cutting portion provided at the end of said working portion is tapered by an angle between 45° and 90°.

6. A horn according to claim 1, wherein said first cutting portion provided at the first edge of said working portion extends parallel to said axis.

7. A horn according to claim 6, wherein said second cutting portion provided at the end of said working portion is tapered by an angle between 45° and 90°.

8. A horn according to claim 6, wherein said second cutting portion provided at the end of said working portion is rounded.

9. A horn according to claim 1, wherein said first cutting portion is provided with a second recess spaced from said first recess by a distance of at least 1.5 mm.

10. A horn according to claim 1, further comprising a second bore spaced from said first bore and extending between said passageway and said first cutting portion.

11. A horn according to claim 10, wherein said working portion is bent with respect to said axis of said horn body by an angle not greater than 90°.

12. A horn according to claim 10, wherein said second cutting portion provided at the end of said working portion is rounded.

13. A horn according to claim 10, wherein said second cutting portion provided at the end of said working portion is tapered by an angle between 45° and 90°.

14. A horn according to claim 10, wherein said first cutting portion provided at the first edge of said working portion extends parallel to said axis.

15. A horn according to claim 14, wherein said second cutting portion provided at the end of said working portion is tapered by an angle between 45° and 90°.

16. A horn according to claim 14, wherein said second cutting portion provided at the end of said working portion is rounded.

17. A horn according to claim 1, further comprising a third cutting portion, said third cutting portion being provided along a second edge of said working portion, said second edge extending generally parallel with said first edge.

18. A horn according to claim 17, further comprising a second recess in said first cutting portion spaced from said first recess by a distance of at least 2 mm, said third cutting portion also being provided with at least one recess.

19. A horn according to claim 1, wherein said recess has a semi-spherical shape having a radius between 0.3 mm and 2.5 mm.

20. A horn according to claim 19, wherein said recess has a depth between 0.1 mm and 2 mm.

21. A horn according to claim 1, further comprising a second recess spaced from said first recess at a distance between 2 mm and 3 mm, and first and second recesses each having a semi-spherical shape with a radius between 0.3 mm and 2.5 mm and a depth between 0.5 mm and 1.5 mm.

* * * * *